(12) United States Patent
Schneider et al.

(10) Patent No.: US 8,703,997 B2
(45) Date of Patent: Apr. 22, 2014

(54) PROCESS FOR PREPARATION AND PREFERABLY DISTILLATIVE WORKUP OF DIPHENYLMETHANE DIISOCYANATE (MDI)

(75) Inventors: Christian Schneider, Mannheim (DE); Nikolaus Zafred, Ludwigshafen (DE); Andreas Heussler, Hassloch (DE); Leo Denissen, Brasschaat (BE); Lucia Koenigsmann, Stuttgart (DE)

(73) Assignee: BASF SE, Ludwigshafen (DE)

( * ) Notice: Subject to any disclaimer, the term of this patent is extended or adjusted under 35 U.S.C. 154(b) by 143 days.

(21) Appl. No.: 13/393,088

(22) PCT Filed: Oct. 20, 2010

(86) PCT No.: PCT/EP2010/065782
§ 371 (c)(1),
(2), (4) Date: Feb. 28, 2012

(87) PCT Pub. No.: WO2011/048134
PCT Pub. Date: Apr. 28, 2011

(65) Prior Publication Data
US 2012/0157709 A1  Jun. 21, 2012

(30) Foreign Application Priority Data
Oct. 20, 2009  (EP) .................................... 09173515

(51) Int. Cl.
*C07C 263/00* (2006.01)
(52) U.S. Cl.
USPC ....................................................... 560/347
(58) Field of Classification Search
None
See application file for complete search history.

(56) References Cited

U.S. PATENT DOCUMENTS 5,877,350 A * 3/1999 Langer et al. ................. 564/423
6,433,219 B1 * 8/2002 Strofer et al. ................. 560/347

FOREIGN PATENT DOCUMENTS

| DE | 1 114 820 | 10/1961 |
| DE | 1 133 394 | 7/1962 |
| EP | 0 696 574 | 2/1996 |
| EP | 0 771 783 | 5/1997 |
| EP | 1 053 222 | 5/2003 |
| WO | 01 64333 | 9/2001 |
| WO | 2008 034770 | 3/2008 |

OTHER PUBLICATIONS

International Search Report Issued Jan. 26, 2011 in PCT/EP10/65782 Filed Oct. 20, 2010.

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

What is proposed is a process for preparation and distillative workup of diphenylmethane diisocyanate (MDI), proceeding from a benzene-comprising feedstream, in which, in
  a catalytic hydrogenation of nitrobenzene to aniline, steam is raised at two different pressure levels, which partly or completely covers the energy demand for the overall process, by using two fluidized bed reactors of identical design, of which
    a first fluidized bed reactor is operated with an aniline load for which the fluidized bed reactors have been designed and provides steam at a first, lower pressure level, and
    a second fluidized bed reactor is operated with a load lowered with respect to the first fluidized bed reactor to such an extent that the second fluidized bed reactor affords steam at the higher pressure level.

10 Claims, No Drawings

PROCESS FOR PREPARATION AND PREFERABLY DISTILLATIVE WORKUP OF DIPHENYLMETHANE DIISOCYANATE (MDI)

The invention relates to a process for preparation and distillative workup of diphenylmethane diisocyanate, referred to hereinafter as MDI for short, proceeding from a benzene-comprising feed stream, in which benzene is nitrated to nitrobenzene which is hydrogenated to aniline, aniline is reacted with formaldehyde to give methylenediphenylamine (MDA) and MDA is phosgenated to MDI. In this process, not the pure products but at first product mixtures are obtained in each process step, which are purified before further processing.

For workup of the product mixtures from the different process stages, the use of steam at two different pressure levels is required. Steam has to date been obtained at a single pressure level from the exothermic process stage, the catalytic hydrogenation of nitrobenzene to aniline. For some of the process steps in the overall process, it was additionally necessary to buy in steam at a higher pressure level from outside the plant.

It was accordingly an object of the invention to provide a process for preparation and distillative workup of MDI proceeding from a benzene-comprising feed stream, which can be operated in an energetically self-sufficient or substantially self-sufficient manner.

The object is achieved by a process for preparation and distillative workup of diphenylmethane diisocyanate (MDI), proceeding from a benzene-comprising feed stream, in which, in process stage I the benzene-comprising feed stream is nitrated to give a nitrobenzene-comprising product mixture, in process stage II the nitrobenzene-comprising product mixture is worked up, preferably by distillation, to obtain a nitrobenzene-comprising feed stream which, in process stage III, is supplied to a hydrogenation to give an aniline-comprising product mixture in a fluidized bed reactor with removal of the heat of reaction by evaporative cooling with water to form steam, in process stage IV the aniline-comprising product mixture is worked up, preferably by distillation, to obtain an aniline-comprising feed stream which, in process stage V, is reacted with formaldehyde in the presence of acidic catalysts to give a methylenediphenylamine (MDA)-comprising stream which, in process stage VI, is purified, preferably by distillation, and, in process stage VII, is supplied to a phosgenation to give an MDI-comprising product mixture which, in process stage VIII, is worked up, preferably by distillation, to give pure MDI, wherein, in process stage III, steam is raised at two different pressure levels, which partly or completely covers the energy demand for process stages IV, VI and VIII, by using two fluidized bed reactors of identical design, of which a first fluidized bed reactor is operated with an aniline load for which the fluidized bed reactors have been designed and provides steam at a first, lower pressure level, and a second fluidized bed reactor is operated with a load lowered with respect to the first fluidized bed reactor to such an extent that the second fluidized bed reactor affords steam at the higher pressure level required for process stages IV, VI and VIII.

Process Stage I

Process stage I, the nitration of a benzene-comprising feed stream to a nitrobenzene-comprising product mixture, is predominantly performed continuously in industry, by combining a mixture of nitric acid and sulfuric acid, known as mixed acid, with benzene. Since the nitration proceeds essentially in the acid phase, the benzene must diffuse from the organic phase into the acid phase, where it reacts with the nitric acid present there to give nitrobenzene.

An industrial scale process for nitrating benzene is described in EP-B 0 771 783, according to which a mixing unit configured as a motive jet nozzle is used, with a central inner tube through which the mixed acid is passed, which functions as the motive jet for the mixing unit and sucks in the benzene-comprising feed stream which is introduced into the ring space surrounding the inner tube.

The process was improved further by BASF SE: according to the BASF process, the reaction is performed adiabatically in a tubular reactor in a large excess of sulfuric acid, the sulfuric acid catalyzing the reaction and functioning as a heat carrier which removes the high heat of reaction released ($\Delta H_R = -117$ kJ·mol$^{-1}$). The temperature rises from originally 90° C. to 135° C. After the reaction, the organic phase is removed from the acidic phase. The sulfuric acid is concentrated and recycled into the process. The nitrobenzene-comprising product mixture, also referred to as crude nitrobenzene, is washed with water and alkali in a mixer-settler cascade in order to neutralize the sulfuric acid still present and remove impurities.

The nitration to nitrobenzene can preferably be performed in a tubular reactor with static mixers, as described in WO 01/64333.

Process Stage II

In process stage II, the nitrobenzene-comprising product mixture is worked up, preferably by distillation, in which case benzene and water are removed as low boilers and a nitrobenzene-comprising feed stream is drawn off, which is fed to process stage III, the catalytic hydrogenation to give an aniline-comprising product mixture.

Process Stage III

In process stage III, the catalytic hydrogenation of a nitrobenzene-comprising feed stream to give an aniline-comprising product mixture is, in accordance with the invention, performed in a fluidized bed reactor.

The industrial scale performance of the process in fluidized bed reactors has already been established for a long time and is described more particularly in German patent DE 1 114 820, and the supplementary patent thereto, DE 1 133 394. The catalytic hydrogenation of nitrobenzene is known to be strongly exothermic, such that maintaining the reaction temperature presents difficulties. The maintenance of the reaction temperature is required especially in order to prevent resinification from occurring on the catalyst and hence the activity of the catalyst from declining within a short time. In order to control these problems, in the process of DE 1 114 820, the reaction is performed in a fluidized bed reactor, wherein the nitrobenzene starting material is supplied in liquid form at a plurality of sites at different heights, and the hydrogen needed for the hydrogenation is supplied together with the nitrobenzene and/or at the base of the fluidized bed reactor. To remove the heat of reaction, a tubular system with a heat carrier circulating therein, especially water, is provided in the fluidized bed reactor. According to the invention, the heat of reaction is removed by evaporative cooling with water, which forms steam. In addition, jacket cooling may also be provided.

In the process according to the main patent DE-A 1 114 820, ambient pressure is employed, from which the process according to the supplementary patent DE-A 1 133 394 departs in employing elevated pressure of at least 3 atmospheres gauge, which is said to achieve a longer lifetime of the catalyst.

Useful catalysts include the heavy metals of groups V to VII of the periodic table and of the iron and platinum groups, for example copper, molybdenum, tungsten, nickel, cobalt or mixtures of these elements, and the oxides, sulfides or halides thereof, optionally together with boron or boron compounds. They may also be applied to supports, such as alumina, natural and synthetic silicates, pumice, iron oxide, magnesia, zinc oxide, zirconium oxide, titanium oxide or thorium oxide. The supports may be treated with bromine, iodine, fluorine or chlorine. The catalyst is employed in the form of grains or powder.

Owing to the very good heat removal properties of the fluidized bed, in which heat flow densities in the range from 10 to 100 kW per square meter can be achieved for removal of heat of reaction, the fluidized bed reactor for the favored isothermal reaction regime can be configured significantly more easily compared to tubular reactors, which have to be cooled in a complex manner.

However, the fluidized bed is found to be disadvantageous with regard to mass transfer, since the formation of gas bubbles of low solids content limits the contact between catalyst and reactants in a known manner. This has the consequence that a portion of the aromatic nitro compounds does not come into contact with the fluidized supported catalyst and leaves the reaction zone unconverted. As a result, not only does the conversion fall but further disadvantages also arise: for example, unconverted nitrobenzene in the aniline is found to be troublesome in the preparation of diphenylmethane diisocyanate (MDI), which is an important intermediate in the polyurethane value addition chain.

Process stage III, the catalytic hydrogenation of nitrobenzene to aniline, is therefore advantageously performed in an improved fluidized bed reactor as proposed in WO 2008/034770, specifically in a fluidized bed reactor in which internals are provided, which divide the fluidized bed into a plurality of cells arranged horizontally and a plurality of cells arranged vertically in the fluidized bed reactor, with cell walls which are gas-pervious and which have orifices which ensure an exchange coefficient of the heterogeneous particulate catalyst in vertical direction in the range from 1 to 100 liters per hour per liter of reactor volume.

Particular preference is given to using, as internals in the fluidized bed, cross-channel packings, i.e. packings with bent gas-permeable metal sheets, expanded metal plies or fabric plies arranged parallel to one another in the fluidized bed reactor in vertical direction, with bend edges which form bend surfaces with a non-zero angle of inclination to the vertical, and wherein the bend surfaces of successive metal sheets, expanded metal plies or fabric plies have the same angle of inclination, but with the opposite sign, thus forming cells bordered in vertical direction by constrictions between the bend edges.

Examples of cross-channel packings are packings of the Mellpak®, CY or BX types from Sulzer AG, CH-8404 Winterthur, or the A3, BSH, B1 or M types from Montz GmbH, D-40723 Hilden.

In the cross-channel packings, cavities form in vertical direction between every two successive metal sheets, expanded metal plies or fabric plies, through the bent structuring thereof, i.e. cells which are bordered by constrictions between the bend edges.

In the fluidized bed reactor, especially in the internals which form cells, are provided heat transferrers in which water circulates as the heat carrier, which absorbs the heat of reaction of the hydrogenation and evaporates as it does so. The heat transferrers may be in plate form or in tubular form and may be arranged vertically, horizontally or inclined in the fluidized bed reactor.

Process Stage IV

The aniline-comprising product mixture obtained in process stage III is worked up, preferably by distillation, in process stage IV to obtain an aniline-comprising feed stream which is reacted in process stage V with formaldehyde in the presence of acidic catalysts to give a methylenediphenylamine (MDA)-comprising stream.

Process Stage V

The preparation of MDA is common knowledge and is effected typically by continuous or batchwise reaction of aniline with formaldehyde in the presence of acidic catalysts. In this reaction, the main product of which is 4,4'-MDA, the undesired N-methyl-MDA by-product is formed to a minor degree. This by-product has an adverse effect especially in the subsequent reaction of the MDA with phosgene to prepare methylenedi(phenyl isocyanate), also referred to as MDI, since the N-methyl-MDA constitutes the precursor compound for chlorinated by-products in the MDI, and minimum chlorine contents in the MDI are desired.

Various processes are known for reduction of the level of N-methyl-MDA as a by-product in the preparation of MDA:

Advantageously, process stage V is performed as described in EP-B 1 053 222, by, in a semicontinuous process, initially charging aniline and optionally acidic catalyst, feeding formaldehyde and optionally acidic catalyst through a mixing unit in a circuit in which aniline, optionally acidic catalyst and optionally formaldehyde which has been added already are moved in circulation, and, after feeding in at least 50% of the total amount of formaldehyde to be fed in, heating the reaction mixture to a temperature of greater than 75° C. This mode of operation allows a higher proportion of higher MDA oligomers to be obtained than is possible with a continuous mode of operation at high molar ratios of aniline to formaldehyde without recycling of the MDA. It is thus possible to minimize the content of undesired by-products.

According to the preferred procedure for process stage V, a crude MDI is obtained with a low content of hydrolyzable chlorine, of less than 0.1%, especially less than 0.045%, and with a light color, expressed by an iodine color number in a dilution of 1:5 in monochlorobenzene of less than 30, more preferably of less than 11.

The process product of process stage V, which is typically also referred to as crude MDA, i.e. a mixture comprising methylenediphenylamine (MDA), for example 2,2'-, 2,4'- and/or 4,4'-MDA as monomeric MDA, and typically polymeric MDA, also known as polymethylenedi(phenylamine), comprises preferably less than 0.09% by weight of N-methyl-MDA.

Process Stage VI

The MDA-comprising stream (crude MDA) obtained in process stage V is worked up in process stage VI, preferably by distillation, and supplied in process stage VII to a phosgenation to give an MDI-comprising stream.

Process Stage VII

The phosgenation can be performed preferably in customary solvents, more preferably in inert solvents, for example chlorinated aromatic hydrocarbons, for example monochlorobenzene, dichlorobenzenes, for example o-dichlorobenzene, p-dichlorobenzene, trichlorobenzenes, the corresponding toluenes and xylenes, chloroethylbenzene, monochlorodiphenyl, alpha- or beta-naphthyl chloride and dialkyl phthalates such as diethyl isophthalate, preferably toluene, mono- and/or dichlorobenzene, in customary reactors, for example stirred tanks, stirred tank cascades, columns and/or tubular reactors at known temperatures of, for example, 50 to 150° C., preferably 70 to 120° C., more preferably 70 to 100° C., and a pressure of 0.5 to 10 bar, preferably 0.8 to 5 bar, more preferably 0.8 to 1.5 bar, in one or more stages. For example, the phosgenation can be performed by a two-stage reaction in the presence of at least one inert organic solvent, the first stage of the phosgenation being performed in a static mixer and the second stage of the phosgenation in a delay time apparatus, the mass ratios of phosgene to hydrogen chloride in the delay time apparatus being simultaneously 10-30:1 in the liquid phase and 1-10:1 in the gas phase.

The static mixers employed for the first stage of the phosgenation are the known apparatuses, especially nozzles.

The temperature in the first stage of the phosgenation is typically 50 to 120° C., preferably 60 to 120° C., more preferably 90 to 120° C.

The delay time apparatuses employed are the known apparatuses, preferably stirring machines, especially stirred tank cascades with 2 to 6 stirred tanks, or columns, especially those having <10 theoretical plates.

In the case of use of stirring machines as delay time apparatuses, as detailed above, especially stirred tank cascades with at least 2, preferably 2 to 6, and more preferably 2 to 5 stirred tanks are used. In principle, a cascade with more than 6 stirred tanks is also usable, but an increase in the number of stirred tanks above 6 merely increases the apparatus complexity without any measurable improvement in the end product. The mixture of the first stage of the phosgenation enters the first stirring machine with a temperature of 70-120° C., preferably 85-105° C. The temperatures in the stirring machines are the same or different in each and are preferably 75-120° C., more preferably 80-110° C. The pressures in the stirring machines are different in each or the same and are typically 1.0-3.0 at gauge, preferably 1.2-2.5 at gauge.

The MDI-comprising product mixture obtained in process stage VII, comprising diphenylmethane diisocyanates (monomeric MDI) and polyphenylenepolymethylene polyisocyanates (polymeric MDI), has typically a diphenylmethane diisocyanate isomer content of 30 to 90% by weight, preferably of 30 to 70% by weight, an NCO content of 29 to 33% by weight, preferably 30 to 32% by weight, based on the crude MDI weight, and a viscosity, determined to DIN 51550 at 25° C., of preferably not more than 2500 mPa·s., preferably of 40 to 2000 mPa·s.

The MDI-comprising product mixture (crude MDI) obtained in process stage VII is worked up in process stage VIII, preferably by distillation, to give pure MDI.

Process Stage VIII

In the present case, pure MDI refers to a mixture comprising at least 98.0% by weight of 4,4'-MDI and additionally not more than 2.0% by weight of 2,4'-MDI, where the acid number, determined to ASTM D1638-74, must not be more than 10 ppm.

The purification, especially by distillation, of the MDI-comprising product mixture obtained in process stage VII may preferably be preceded by a stripping process in which phosgene and any solvents are removed from the crude MDI.

In such a stripping process, the crude MDI can be passed into one or more apparatuses with large internal surface area, on the surface of which it is distributed such that readily volatile components can escape. The apparatus may comprise, for example and with preference, a falling-film or thin-film evaporator or a packed column of suitable design. Inert gases can be fed in as a stripping medium and/or reduced pressure can be applied over the apparatus. The temperatures during this stripping process are preferably below 210° C., more preferably 50 to 190° C.

Subsequently, in process stage VIII, pure MDI is obtained by distillation, for example at pressures of 2 to 50 mbar, preferably 2 to 20 mbar, and temperatures of 150 to 250° C., preferably 180 to 230° C., more preferably 210 to 230° C.

The pure MDI is subsequently typically stabilized with an antioxidant based on sterically hindered phenols and/or at least one aryl phosphite.

According to the invention, the strongly exothermic process stage III, the catalytic hydrogenation of nitrobenzene to give an aniline-comprising product mixture, is utilized in a technically simple, elegant manner in order to provide steam at two different pressure levels, and hence operate the entire plant, comprising all process stages I to VIII, in an energetically self-sufficient or substantially self-sufficient manner.

The complex design of the fluidized bed reactors which are used for the catalytic hydrogenation of nitrobenzene must be undertaken only once in the process according to the invention, since it has been found that it is possible to provide, in a simple manner, steam at two different pressure levels by operating a first fluidized bed reactor at full load, i.e. at the load for which it was designed, and a second fluidized bed reactor merely with a partial load. This generates a smaller amount of heat Q at the same reaction temperature $T_R$, unchanged heat transfer coefficient k and equal heat transfer area A, and hence the temperature of the heat carrier $T_W$ removing the heat of reaction and, correspondingly, the vapor pressure thereof are higher.

The above relationships can be illustrated by the equation $$Q = k \cdot A \cdot (T_R - T_W)$$

in which

Q is the amount of heat generated in the reactor by the catalytic hydrogenation, k is the heat transfer coefficient, A is the heat transfer area, $T_R$ is the reaction temperature and $T_W$ is the temperature of the heat transferrer.

The amount of heat Q is directly proportional to the production capacity of the reactor.

The heat transfer coefficient k is determined by the catalyst properties and varies in the range from about 500 W/m²·K to approx. 1000 W/m²·K. In general, the k value rises with increasing catalyst service life, especially as a result of coking of the catalyst and the associated increase in the particle density.

In a preferred process variant, this can be utilized by filling the two fluidized bed reactors with catalysts which have already been in use for different lengths of time, specifically by operating the fluidized bed reactor filled with fresher catalyst at a load which leads to raising of steam at the lower pressure level, and the fluidized bed reactor filled with the catalyst which has already been in use for a longer period at a load which leads to raising of steam at a higher pressure level.

According to the invention, two fluidized bed reactors of identical design are set up, though apparatuses "of identical design" are not understood to mean apparatuses identical in all details but merely essentially identical apparatuses, especially apparatuses with equal heat transfer areas A.

The reaction temperature $T_R$ in the fluidized bed reactors is regulated especially to a value in the range from approx. 280 to 320° C., preferably to a value in the range from approx. 290 to 300° C.

Preferably, the water for the removal of the heat of reaction from the fluidized bed reactor is supplied via a steam drum to a tube bundle heat exchanger arranged in the interior of the fluidized bed reactor, and the steam which arises from the absorption of the heat of reaction by evaporative cooling in the tube bundle heat exchanger is discharged via a regulating valve by which the steam pressure is regulated to the first or second pressure level.

Preferably, the first pressure level is regulated to a value in the range from about 16 to 30 bar absolute.

If required, instead of a single first or second fluidized bed reactor, it is possible in each case to use two or more fluidized bed reactors.

It is also possible to switch the fluidized bed reactors, each of which provides steam at a lower or higher pressure level, flexibly between the two modes of operation by suitable technical measures during ongoing operation.

Furthermore, it is also possible with the existing plant to react flexibly to aniline demand, by increasing the aniline load of the fluidized bed reactor which has previously been utilized to raise steam at a higher pressure level, and instead to buy in steam at a higher pressure level from outside.

The invention is illustrated in detail by a working example.

On the basis of the above-specified equation for the amount of heat generated in the catalytic hydrogenation of nitrobenzene, $$Q = k \cdot A \cdot (T_R - T_W)$$

a required heat exchange area of 600 m² is calculated for a reactor with a target production capacity of 120 kt/a and with heat of reaction to be removed of 15.9 MW, a reactor temperature of 280° C., a heat transfer coefficient k of 550 W/m²·K and a steam drum pressure of 30 bar absolute.

A second fluidized bed reactor with the same heat transfer area of 600 m² is operated with correspondingly higher steam drum pressure, specifically 42 bar absolute, in order to ensure steam supply into process stages IV, VI and VIII. Owing to the relatively small temperature difference between catalyst bed and heat transferrer, a smaller amount of heat can be removed, of 10.5 MW, and the second fluidized bed reactor can correspondingly be operated only with a lower capacity, of 80 kt/a, i.e. with a partial load.

Thus, by operating two fluidized bed reactors with equal heat transfer area, of 600 m² in each case, a first reactor being operated at full load and a second at partial load, steam is obtained at two pressure levels, specifically of 30 bar absolute and 40 bar absolute steam.

The invention claimed is:

1. A process for preparation and distillative workup of diphenylmethane diisocyanate (MDI), the process comprising:
   (I) nitrating a benzene-comprising feedstream to give a nitrobenzene-comprising product mixture;
   (II) purifying the nitrobenzene-comprising product mixture to obtain a nitrobenzene-comprising feedstream;
   (III) catalytically hydrogenating the nitrobenzene-comprising feedstream to give an aniline-comprising product mixture, wherein the hydrogenating occurs in at least two fluidized bed reactors with water for removal of heat of reaction by evaporative cooling to form steam;
   (IV) purifying the aniline-comprising product mixture to obtain an aniline-comprising feedstream;
   (V) reacting the aniline-comprising feedstream with formaldehyde in the presence of at least one acidic catalyst to give a methylenediphenylamine (MDA)-comprising stream;
   (VI) purifying the methylenediphenylamine (MDA)-comprising stream to give a purified methylenediphenylamine (MDA)-comprising stream;
   (VII) phosgenating the purified methylenediphenylamine (MDA)-comprising stream to give an MDI-comprising product mixture; and
   (VIII) purifying the MDI-comprising product mixture to give a purer MDI,
   wherein:
   the at least two fluidized bed reactors in the hydrogenating (III) are of identical design;
   the hydrogenating (III) comprises operating a first fluidized bed reactor with a full aniline load and the first fluidized bed reactor provides steam at a first, pressure level;
   the hydrogenating (III) further comprises operating a second fluidized bed reactor with a load lowered with respect to the first fluidized bed reactor to such an extent that the second fluidized bed reactor affords steam at a second pressure level, which is higher than the first pressure level and is required for the purifying (IV), the purifying (VI), and the purifying (VIII); and
   the purifying (IV), the purifying (VI), and the purifying (VIII) each comprises purifying with energy provided by the steam obtained from the second fluidized bed reactor.

2. The process of claim 1, wherein the water for the removal of the heat of reaction is supplied from a steam drum to a tube bundle heat exchanger arranged in the interior of the at least two fluidized bed reactors, and steam which arises from absorption of the heat of reaction by evaporative cooling in the tube bundle heat exchanger is discharged through a regulating valve by which steam pressure is regulated to the first or second pressure level.

3. The process of claim 1, wherein the first pressure level is regulated to a pressure in a range of from 16 to 30 bar absolute, and the second higher pressure level to >40 bar absolute.

4. The process of claim 1, wherein a reaction temperature in the fluidized bed reactors is regulated to a value in a range of from 280 to 320° C.

5. The process of claim 4, wherein the reaction temperature in the fluidized bed reactors is regulated to a value in a range of from 290 to 300° C.

6. The process of claim 1, wherein the at least two fluidized bed reactors are filled with catalysts which have already been in use for different lengths of time, such that a fluidized bed reactor filled with a fresher catalyst is operated at a load forming steam at the first pressure level, and a fluidized bed reactor filled with a catalyst having been in use for a longer period is operated at a load forming steam at the second pressure level.

7. The process of claim 1, wherein the purifying (VI) is carried out by distillation.

8. The process of claim 1, wherein the purifying (VIII) is carried out by distillation.

9. The process of claim 1, wherein the purifying (II) is carried out by distillation.

10. The process of claim 1, wherein the purifying (IV) is carried out by distillation.

\* \* \* \* \*